United States Patent [19]

Takizawa et al.

[11] 4,396,260
[45] Aug. 2, 1983

[54] SLIT LAMP HAVING REPLACEABLE OBJECTIVE LENS UNIT FOR OBSERVATION OF CORNEA

[75] Inventors: Shiro Takizawa; Shinichi Nishimura, both of Tokyo, Japan

[73] Assignee: Tokyo Kogaku Kikai Kabushiki Kaisha, Japan

[21] Appl. No.: 122,673

[22] Filed: Feb. 19, 1980

[30] Foreign Application Priority Data

Feb. 20, 1979 [JP] Japan .................................. 54-18711

[51] Int. Cl.³ ........................... A61B 3/14; A61B 3/10
[52] U.S. Cl. ..................................... 351/206; 351/214
[58] Field of Search .................... 351/7, 14, 206, 214; 354/62; 350/19, 39, 33, 34

[56] References Cited

U.S. PATENT DOCUMENTS

| | | | |
|---|---|---|---|
| 2,622,473 | 12/1952 | Littmann | 351/14 X |
| 3,173,984 | 3/1965 | Vogl | 350/39 |
| 3,652,153 | 3/1972 | Gambs | 351/14 |
| 4,132,466 | 1/1979 | Matsumura | 351/14 |

Primary Examiner—John K. Corbin
Assistant Examiner—Rodney B. Bovernick
Attorney, Agent, or Firm—Brumbaugh, Graves, Donohue & Raymond

[57] ABSTRACT

Slit lamp having a slit illumination system, a binocular microscopic system and a photographing system. The binocular microscopic system has an objective lens assembly which is mounted replaceably on the body. A replaceable lens unit is provided for observation of the endothelial cell of the cornea. The lens unit include an objective lens, a relay lens and mirrors for directing the light bundle through the objective lens to one of the optical paths in the binocular microscopic system.

4 Claims, 4 Drawing Figures

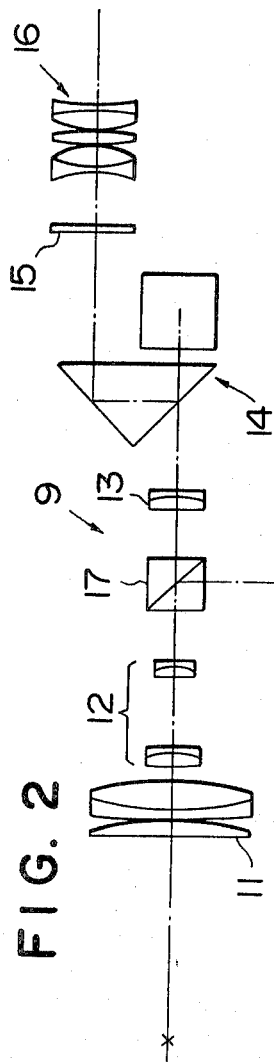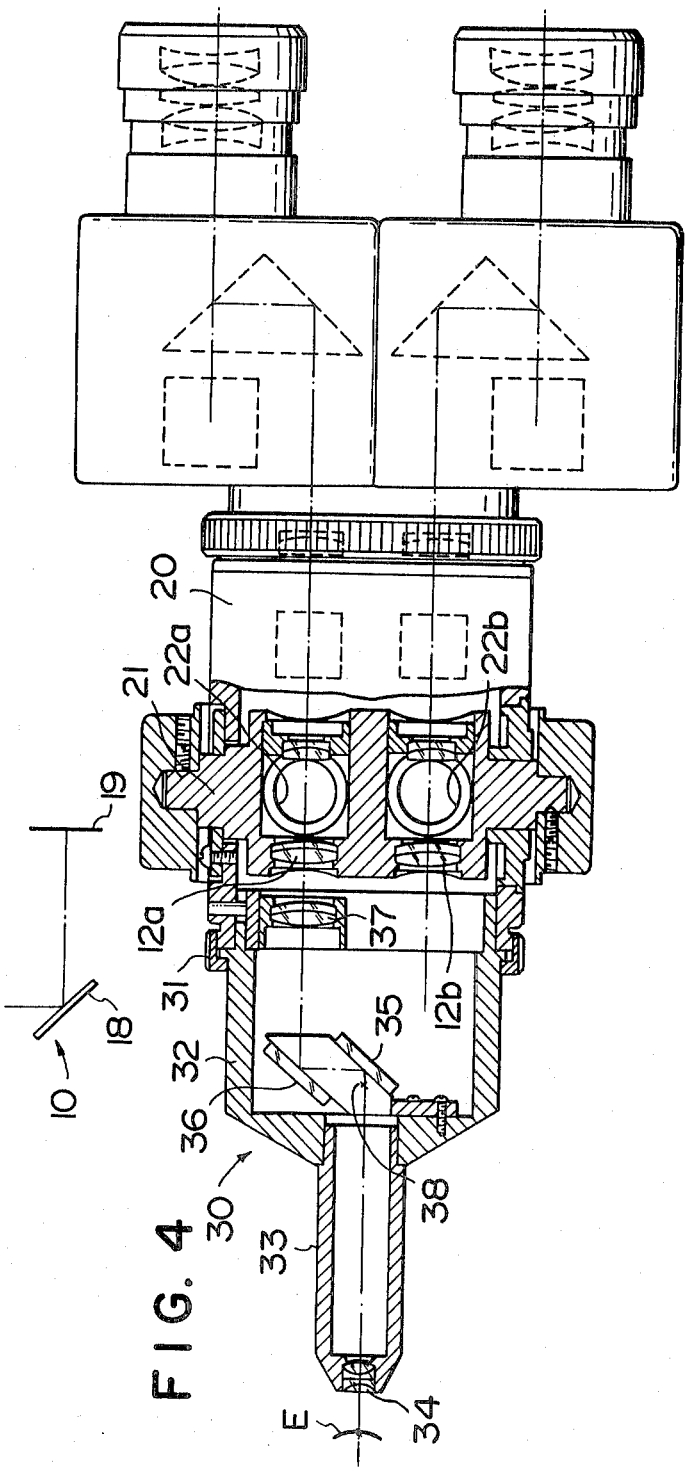

SLIT LAMP HAVING REPLACEABLE OBJECTIVE LENS UNIT FOR OBSERVATION OF CORNEA

TECHNICAL FIELD OF THE INVENTION

This invention relates to a slit lamp and specifically to a slit lamp which makes it possible to observe the endothelial cell of the cornea.

BACKGROUND OF THE INVENTION

On the back of the cornea of a human eyeball, there is a cellular film called an endothelial cell which consists of tortoise shell-shaped cells having a size of about 20 microns and which plays the most important role in maintaining the transparency of the cornea. Hence, it is believed to be of the utmost importance to observe and photograph the endothelial cell in vivo. In performing the transplantation of the cornea, for example, it is important to know the conditions of the endothelial cell of the cornea to be transplanted. It is also important to observe the corneal endothelial cell in order to confirm the results of the surgical operation after the transplantation. The observation and examination of the corneal endothelial cell is also necessary to determine the influence of an instrument or an artificial lens on the cell when they are inserted into the eyeball in performing a surgical operation on a cataract.

The endothelial cell film of the cornea is as transparent as the corneal substrate and the contrast with its surroundings is so weak that observation with an ordinary microscope is rather difficult. For this reason, a specific illumination method has been employed. In other words, a thin slit luminous flux is used for illumination and the optical axis of illumination must be arranged at a suitable angle relative to the optical axis for observation and photography lest the reflected ray of light on the corneal surface enter the photographing system.

Conventional apparatuses produced for this purpose are broadly classified into two groups. One is the type in which the illumination system and the observation and photographing system use an objective lens in common, and the other in which both systems have respective separate objective lenses. In any case, magnification of at least about 100 times is necessary for the observation of the corneal endothelial cell and magnification of about 20 times is necessary for taking a photograph. For this reason, the conventional apparatuses have been produced exclusively for the purpose of observing and photographing the endothelial cell of the cornea, and they are expensive and call for a high level skill for their operation.

SUMMARY OF THE INVENTION

The present invention has an object to enable a slit lamp to be used also for the observation of the corneal endothelial cell simply by interchanging an objective lens system. For the purpose, the present invention is characterized in that an objective lens system in the optical system of a binocular stereoscopic microscope which is the observation-photography system of the slit lamp, is made interchangeable and as the interchangeable objective lens unit, use is made of a unit including an objective lens for allowing the luminous flux from the slit illumination portion to temporarily form an image, a relay lens for relaying said luminous flux and an optical element for guiding the luminous flux from the relay lens to one of a pair of observation optical paths of the binocular stereoscopic microscope system.

In the interchangeable objective lens unit, the objective lens is furnished with a magnification of about 5X and the focal length of the relay lens is made sufficiently short, thereby making it possible to easily obtain a required magnification. Further, the imaging point of the objective lens is placed on the focal plane of the relay lens so that the luminous flux leaving the relay lens is converted into parallel rays and the optical system subsequent thereto can be used as such.

In order to increase the magnification on the basis of the optical system of the conventional slit lamp, the taking relay lens of the photography system may be elongated or the focal length of the objective lens may be shortened. However, the former method involves a problem wherein though the magnification can be increased, the resolution can not be increased correspondingly. In the latter, there is an inherent limit to the shortening of the focal length because if it is made too short, the objective lens mechanically intereferes with the slit illumination system whereby it becomes difficult to maintain a suitable angle between the optical axis for observation and photography and the optical axis for illumination.

As explaned above, the present invention uses the interchangeable lens unit consisting of the objective lens, the relay lens and the optical element which leads the luminous flux to one of the optical paths of the binocular stereoscopic microscope system, and this interchangeable lens unit is made interchangeable with the objective lens system of the ordinary slit lamp, thereby making it possible to obtain the necessary magnification.

BRIEF DESCRIPTION OF THE DRAWING

The above and other objects and features of the present invention will become apparent from the following descriptions of a preferred embodiment taking reference to the accompanying drawings, in which;

FIG. 2 is a side view of the abovementioned example;

FIG. 4 is a partially cut-away plan view showing the construction of FIG. 3 on which the objective lens unit in accordance with the present invention is mounted.

DETAILED DESCRIPTION OF THE PREFERRED EMBODIMENT

Figure 1:
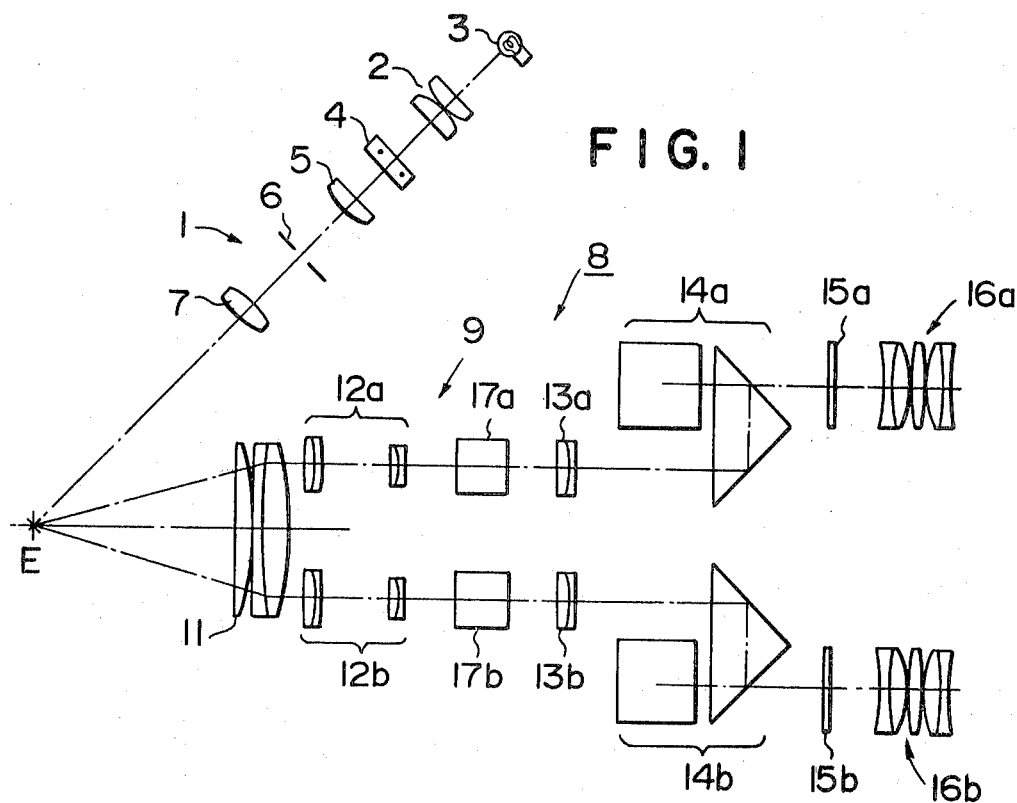
FIG. 1 is a plan view showing an example of the optical system of the slit lamp.

Hereinafter, an embodiment of the present invention will be explained by referring to the accompanying drawings. FIGS. 1 and 2 are a plan view and a side view showing the outline of the optical system of the slit lamp, respectively. An illumination system 1 includes a light source 3 for observation and a light source 4 for photography that are located at conjugate positions with each other to interpose lenses 2 between them. The ray of light from these light sources 3 and 4 is projected onto the eye E to be examined by means of an objective lens 7 through a lens 5 and a slit diaphragm 6.

An optical system 8 for observation and photography consists of a binocular stereoscopic microscope system 9 and a photography system 10. The binocular stereoscopic microscope system 9 includes a common objective lens 11 and variable power lenses 12a and 12b that are placed at the back of the objective lens 11 and form a pair of parallel optical paths. The rays of light passing through the variable power lenses 12a, 12b then pass through lenses 13a, 13b and erecting Porro prisms 14a, 14b and form images on imaging faces 15a, 15b, which are observed through oculars 16a, 16b, respectively. A photography system 10 includes half mirrors 17a, 17b that are interposed between the lenses 12a, 12b and the lenses 13a, 13b, respectively, and these half mirrors 17a, 17b reflect downward a part of the luminous flux passing through the variable power lenses 12a, 12b. The luminous flux thus reflected is further reflected rearward by a mirror 18 and forms an image on the surface 19 of a film for taking a photograph.

Figure 3:
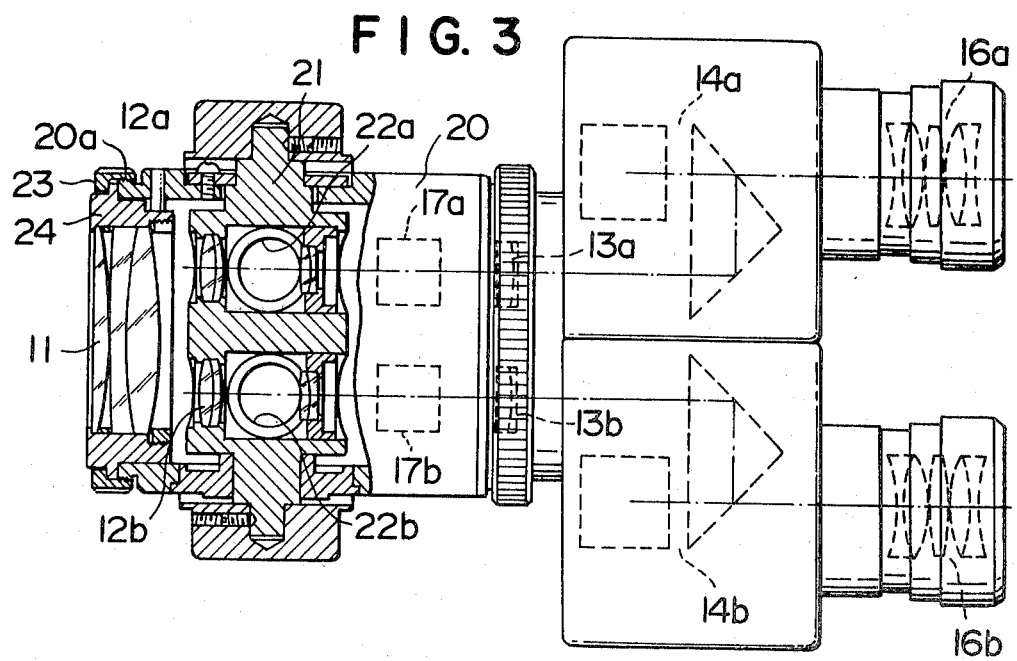
FIG. 3 is a partially cut-away plan view showing the detailed construction of a binocular stereoscopic microscope system.

FIG. 3 shows the detailed construction of the binocular stereoscopic microscope system 9, wherein the variable power lenses 12a, 12b are fitted onto a rotary member 21 which is turnably fitted onto a lens-barrel 20 around an axis which is at right angles to the optical axis. When this rotary member 21 is manipulated for rotation, the variable power lenses 12a, 12b and through-apertures 22a, 22b defined on the rotary member 21 are alternately inserted into the optical path for observation and photography. The objective lens 11 is fitted to a lens frame 24 that is detachably mounted on the lens-barrel 20 by means of a ring nut 23 engaging with a male screw portion 20a at the tip of the lens-barrel 20.

FIG. 4 shows the state where the objective lens 11 shown in FIG. 3 is removed from the lens-barrel and replaced by an objective lens unit 30 for the observation of the corneal endothelial cell. This lens unit 30 includes a case 32 detachably fitted to the tip of the lens-barrel 20 by means of a ring nut 31 and a lens-barrel 33 having a small diameter, fixed to the abovementioned case 32 and protruding forward. An objective lens 34 is fitted to the tip of this lens-barrel 33. Inside the case 32 are disposed mirrors 35 and 36 for guiding the ray of light, which is incident along the optical axis of the objective lens 34, along one of the optical axis of the binocular stereoscopic microscope system. Inside the case, further, a relay lens 37 is disposed at the back of the mirror 36. Since the objective lens 34 has a focal distance of 10 mm and magnification of 5X, for example, and the ray of light passing through this lens 34 temporarily forms an image at a point indicated by 38, and since the relay lens 37 has a focal length of 50 mm and a focal point so located as to be superimposed on the above-mentioned imaging point 38, for example, the rays of light passing through the latter lens 37 become parallel. Accordingly, it is possible to use the optical system of the slit lamp itself as the subsequent optical system.

We claim:

1. Slit lamp including a slit illumination system for projecting a slit luminous flux to a patient's eye, a body provided with a mount, objective lens means adapted to be mounted through said mount on said body so that it can be easily replaced, a binocular microscopic system including a pair of optical paths for observing an illuminated portion of the patient's eye through said objective lens means, a pair of variable power lenses for varying the magnification of the image observed, said pair of variable power lenses being placed between said objective lens and said observing optical paths, a photographing optical system for taking photographs of said illuminated portion of the patient's eye, said photographing system having at least one optical path which is at least partially in common with said binocular optical system, and an alternative lens means for observing the ocular anterior of the patient's eye in high magnification, said alternative lens means being replaceably mountable through said mount on said body in lieu of said objective lens means, said alternative lens means including alternative objective lens means for focusing a beam of light at an image point, relay lens means for relaying said beam of light from said image point and optical means for directing the beam of light to one of the variable power lenses in the binocular microscopic system.

2. Slit lamp in accordance with claim 1 in which said photographing optical system includes a pair of optical paths which respectively correspond to the observing optical paths.

3. Slit lamp in accordance with claim 1 in which said optical means includes reflective mirror means.

4. Slit lamp in accordance with claim 1 having mirror means for directing light into said photographing system comprising a pair of parallel mirrors having reflective surfaces opposed to each other and inclined with respect to an optical axis of the objective lens.

* * * * *